(12) United States Patent
    Wittenberger

(10) Patent No.: US 9,539,046 B2
(45) Date of Patent: Jan. 10, 2017

(54) CRYOGENIC MEDICAL MAPPING AND TREATMENT DEVICE

(75) Inventor: Dan Wittenberger, L'ile Bizard (CA)

(73) Assignee: Medtronic CryoCath LP, Toronto, Ontario (CA)

(*) Notice: Subject to any disclaimer, the term of this patent is extended or adjusted under 35 U.S.C. 154(b) by 1240 days.

(21) Appl. No.: 12/849,468

(22) Filed: Aug. 3, 2010

(65) Prior Publication Data

US 2012/0035601 A1    Feb. 9, 2012

(51) Int. Cl.
    *A61B 18/18*   (2006.01)
    *A61B 18/02*   (2006.01)
    *A61B 18/14*   (2006.01)
    *A61B 18/00*   (2006.01)

(52) U.S. Cl.
    CPC ......... *A61B 18/02* (2013.01); *A61B 18/1492* (2013.01); *A61B 2018/0022* (2013.01); *A61B 2018/00375* (2013.01); *A61B 2018/00839* (2013.01); *A61B 2018/0212* (2013.01); *A61B 2018/1497* (2013.01)

(58) Field of Classification Search
    CPC ............ A61B 18/02; A61B 2018/0212; A61B 2018/0262; A61B 2018/00214; A61B 2018/0022; A61B 2018/1405; A61N 5/00; A61N 2005/002
    USPC .............. 606/20–26, 34, 35, 41–49; 607/96, 607/98–102, 104–106
    See application file for complete search history.

(56) References Cited

U.S. PATENT DOCUMENTS

| 5,398,683 | A | 3/1995 | Edwards et al. |
| 5,617,854 | A | 4/1997 | Munsif |
| 5,871,483 | A * | 2/1999 | Jackson et al. ................ 606/41 |
| 6,073,052 | A * | 6/2000 | Zelickson et al. ............. 606/41 |
| 6,088,614 | A | 7/2000 | Swanson |
| 6,164,283 | A | 12/2000 | Lesh |
| 6,738,673 | B2 | 5/2004 | Desai |
| 7,519,410 | B2 | 4/2009 | Taimisto et al. |
| 7,540,853 | B2 | 6/2009 | Hayzelden |
| 7,655,005 | B2 | 2/2010 | Bhola |

(Continued)

FOREIGN PATENT DOCUMENTS

| CN | 1259852 A | 7/2000 |
| CN | 1652728 A | 8/2005 |

(Continued)

OTHER PUBLICATIONS

The State Intellectual Property Office of the People's Republic of China, Notice on the First Office Action and Search Report, Aug. 20, 2014, 12 pages for Application No. 201180038095.0.

*Primary Examiner* — Ahmed Farah
(74) *Attorney, Agent, or Firm* — Christopher & Weisberg, P.A.

(57) ABSTRACT

A medical device and method are provided for mapping and therapeutic treatment, which may include a source of cryogenic fluid, a balloon or other expandable member in fluid communication with the source of cryogenic fluid, and a plurality of electrodes on the expandable member. The medical device may include a catheter or elongate body, and the electrodes may take the form of longitudinal strips. The expandable member may take the form of an inner and outer balloon, and the electrodes may be on the outer balloon. The electrodes may be on a proximal or distal conical portion of the expandable member, or both. An electrical insulator may be provided covering a portion of the electrodes.

6 Claims, 8 Drawing Sheets

(56) References Cited

U.S. PATENT DOCUMENTS

| | | |
|---|---|---|
| 2002/0035361 A1 | 3/2002 | Houser et al. |
| 2004/0082950 A1* | 4/2004 | Edwards et al. ............... 606/41 |
| 2005/0256521 A1 | 11/2005 | Kozel |
| 2008/0281391 A1 | 11/2008 | MacAdam et al. |
| 2009/0076494 A1* | 3/2009 | Azure ............................ 606/33 |
| 2009/0192508 A1* | 7/2009 | Laufer et al. .................. 606/41 |
| 2009/0228003 A1 | 9/2009 | Sinelnikov |
| 2009/0248014 A1 | 10/2009 | Shachar et al. |
| 2009/0299355 A1* | 12/2009 | Bencini et al. ................ 606/21 |

FOREIGN PATENT DOCUMENTS

| | | |
|---|---|---|
| CN | 101309651 A | 11/2008 |
| CN | 101355912 A | 1/2009 |
| EP | 1383426 B1 | 12/2008 |
| WO | 9406349 A1 | 3/1994 |
| WO | 9902096 A1 | 1/1999 |
| WO | 0122897 A1 | 4/2001 |
| WO | 02083196 A2 | 10/2002 |
| WO | 2005067668 A2 | 7/2005 |
| WO | 2006118725 A1 | 11/2006 |
| WO | 2009065042 A2 | 5/2009 |
| WO | 2009140067 A1 | 11/2009 |

\* cited by examiner

CRYOGENIC MEDICAL MAPPING AND TREATMENT DEVICE

CROSS-REFERENCE TO RELATED APPLICATION

N/A

STATEMENT REGARDING FEDERALLY SPONSORED RESEARCH OR DEVELOPMENT

N/A

FIELD OF THE INVENTION

The present invention relates to medical systems and methods for electrophysiological procedures and treatment, and in particular to tissue mapping and ablation.

BACKGROUND OF THE INVENTION

Medical procedures are available for treating a variety of cardiovascular maladies, such as cardiac arrhythmias including atrial fibrillation, and other irregularities in the transmission of electrical impulses through the heart. As an alternative to open-heart surgery, many medical procedures are performed using minimally invasive surgical techniques, where one or more slender implements are inserted through one or more small incisions into a patient's body. Such procedures may involve the use of catheters or probes having multiple sensors, electrodes, or other measurement and treatment components to treat the diseased area of the heart, vasculature, or other tissue. Minimally-invasive devices are desirable for various medical and surgical applications because they allow for precise treatment of localized discrete tissues that are otherwise difficult to access. For example, catheters may be easily inserted and navigated through the blood vessels and arteries, allowing non-invasive percutaneous access to areas of the body selected for treatment, while other minimally-invasive probes or instruments may be inserted into small openings and directed through targeted anatomy without significant impact or disruption to surrounding tissue.

One such example of a minimally invasive therapy involves the treatment of cardiac arrhythmias or irregular heartbeats in which physicians employ specialized cardiac assessment and treatment devices, such as mapping catheters and ablation catheters, to gain access to, diagnose, and treat interior regions of a patient's body. Such devices may include energized electrodes or other ablation assemblies to create lesions or other anatomical effects that disrupt or block electrical pathways through the targeted tissue.

In the treatment of cardiac arrhythmias, a specific area of cardiac tissue having aberrant electrically conductive pathways is typically initially identified for subsequent treatment. This localization or identification can include first using a medical device such as a mapping catheter to obtain a baseline electrophysiological map of electrical activity in selected tissue. After mapping and diagnosing aberrant tissue, a physician may decide to treat the patient by ablating the tissue. An ablation procedure may involve creating one or more lesions to electrically isolate tissue believed to be the source of an arrhythmia. One type of ablation is the cryotreatment or cryogenic ablation, which entails creating cold temperatures at specific regions of the body or contacting tissue with cold treatment devices to transfer heat from the targeted tissue to the cryogenic element, thus cooling and/or ablating the tissue.

Such cryotreatment may require first repositioning or removing a mapping catheter before placing a second medical device or ablation catheter into contact with the tissue to be treated. Following the ablation procedure, the physician may desire to asses or confirm the efficacy of the treatment by obtaining a second electrophysiological map of the tissue region. This subsequent mapping procedure may involve removal or manipulation of the ablation medical device to allow the desired positioning of the mapping device adjacent to the tissue that was previously treated.

Each device exchange or manipulation represents an added risk to the patient as inserting and removing catheters in the vasculature carries a number of inherent risks, possibly including embolism. Exchanging these various catheters during a procedure can cause inaccuracies or movement in the placement and location of the distal tip a device with respect to the tissue to be mapped or ablated, and may further add to the time required to perform the desired treatment. These potential inaccuracies and extended duration of the particular procedure further increase the risk to the patient undergoing treatment. Accordingly, it would be desirable to provide an integrated apparatus and method of use thereof for both diagnosing aberrant electrical pathways and treating those detected pathways.

In addition, placing and maintaining a medical device in the desired position with correct alignment and positive contact with the selected tissue may enhance a mapping and ablation treatment and its likelihood of success. It is therefore desirable to provide apparatus and method of use to verify the position of a medical device, positive contact and alignment with the selected tissue, and to evaluate the medical treatment contemporaneously.

SUMMARY OF THE INVENTION

The present invention advantageously provides a medical device and method for treating a patient by mapping and cryogenic treatment. In particular, a medical device may include an elongate body defining a fluid flow path, an expandable member coupled to the elongate body in fluid communication with the fluid flow path, a cryogenic fluid source in fluid communication with the fluid flow path, and a plurality of electrodes on the expandable member.

The expandable member may be a balloon, or may be a first balloon inside a second balloon with the electrodes being on the second balloon. The electrodes may extend between a distal position and a proximal position on the expandable member, and may be arranged at different angular positions around a longitudinal axis of the expandable member. A balloon in an expanded configuration may have a shape with a distal conical portion and a proximal conical portion. An effective portion of the electrodes may be limited to a proximal conical portion, a distal conical portion, or both portions, and may be at different longitudinal positions on the expandable member. The electrodes may have the shape of longitudinal strips, and their distal ends may be proximal of a distal end of the expandable member. An electrical insulator may also be provided, covering a portion of the electrode.

A medical device is also provided which may include a source of cryogenic fluid, a balloon in fluid communication with the source of cryogenic fluid, and a plurality of electrodes on the balloon, in which each electrode is at a different longitudinal position on the expandable member.

A method of medical treatment is also provided, including expanding an expandable member and a plurality of electrodes on the expandable member into contact with tissue to be treated, ablating the tissue by energy transfer between the expandable member and the tissue, and obtaining signals from the electrodes to evaluate electrical activity in the tissue. The method may also include maintaining the expandable member and the electrodes in a contact position while ablating the tissue and obtaining the signals. The method may include ablating the tissue and obtaining signals from the electrodes simultaneously. The method may also include calculating an average rate of change of the signals during ablating the tissue, and ceasing ablation if the average rate of change is below a predetermined threshold. The method may also include calculating an average variance of a rate of change of the signals during ablating the tissue, and ceasing ablation if the average variance exceeds a predetermined threshold. The method may also include contacting the tissue to be treated with a distal portion of the expandable member, or advancing the expandable member through a septum and contacting the tissue to be treated with a proximal portion of the expandable member.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Figure 1:
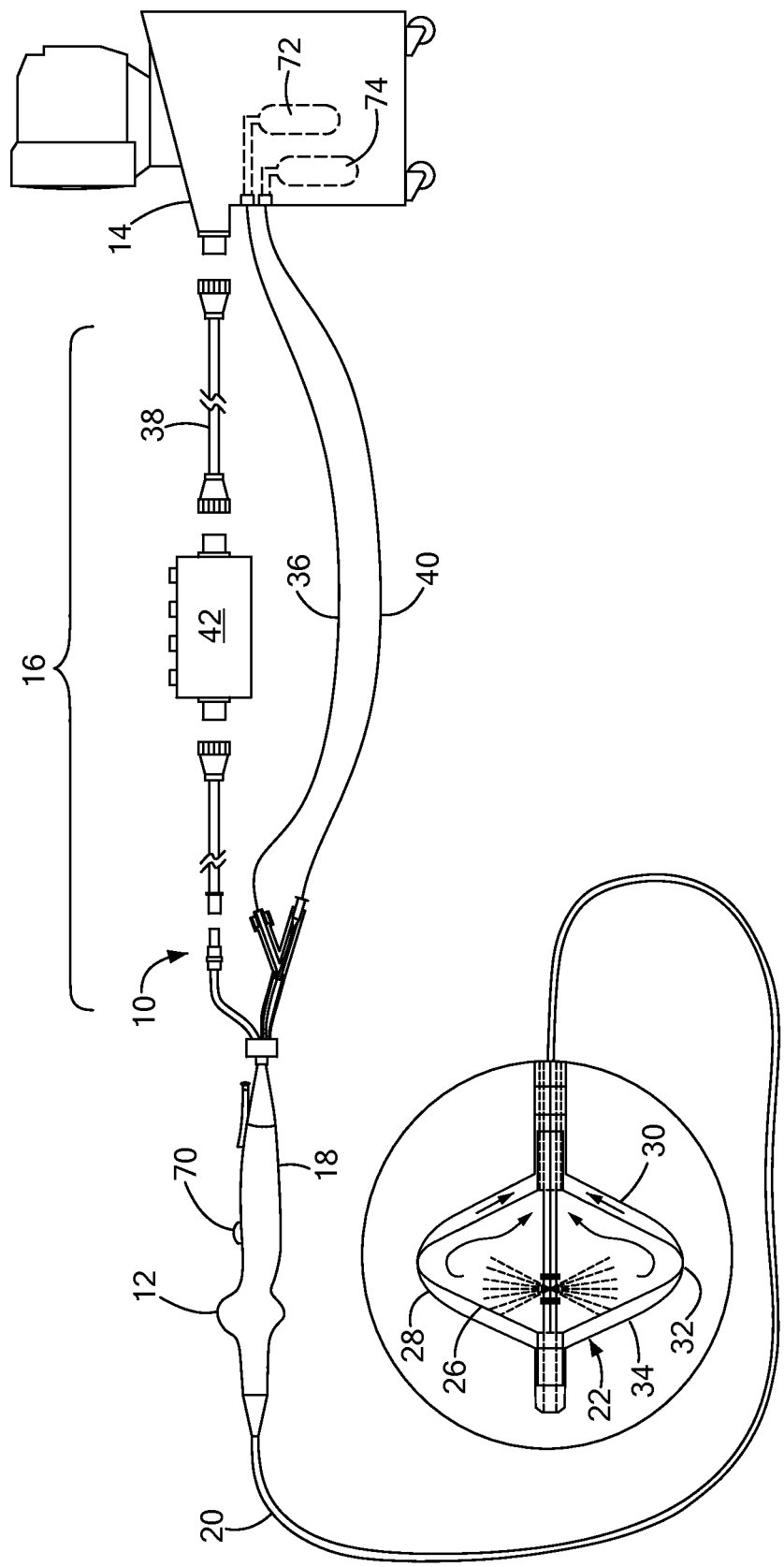
FIG. 1 is an illustration of an exemplary medical system constructed in accordance with the principles of the present invention.

The present invention provides medical devices, systems and methods of use thereof to perform medical diagnoses and treatments including electrophysiological mapping and cryogenic ablation. Referring now to the drawings in which like reference designators refer to like elements, there is shown in FIG. 1 an exemplary embodiment of a medical system for diagnosing and treating tissue, such as cardiac or other vascular tissue, designated generally as 10. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein may be included in a variety of different combinations or configurations without departing from the scope and spirit of the invention.

As shown in FIG. 1, the system 10 generally includes a medical device 12 coupled to a cooling unit or console 14 through an umbilical system 16. The medical device 12 may be a medical probe, a catheter, a balloon catheter, or any other device deliverable or otherwise positionable through the vasculature and/or proximate to a tissue region selected for treatment, including cardiac or vascular tissue. Such treatments may include for example mapping electrical activity of various tissues, thermal ablation of tissue selected for treatment, and subsequent mapping to assess or confirm treatment efficacy.

Figure 2:
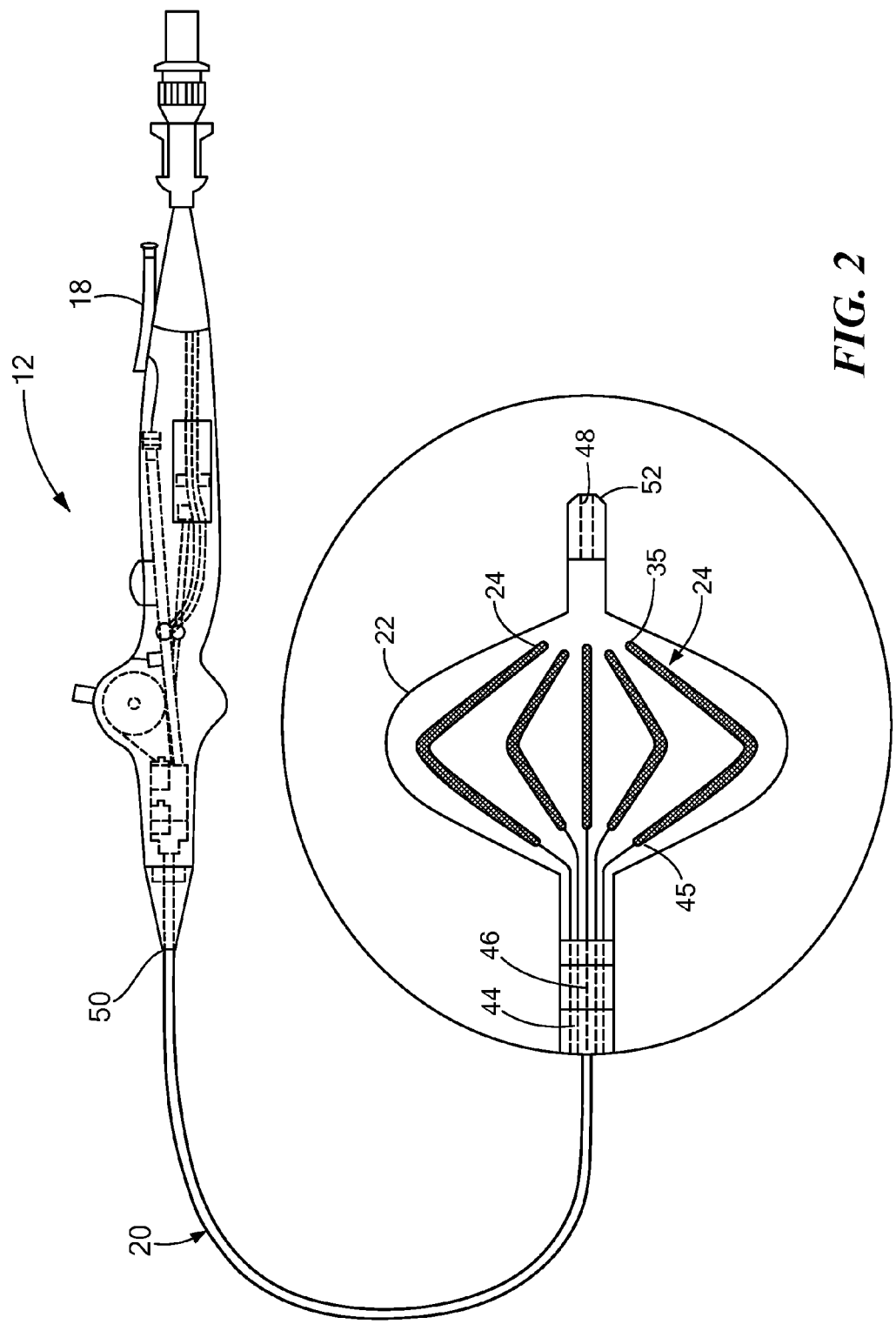
FIG. 2 is an illustration of an exemplary medical device constructed in accordance with the principles of the present invention.
Figure 3A:
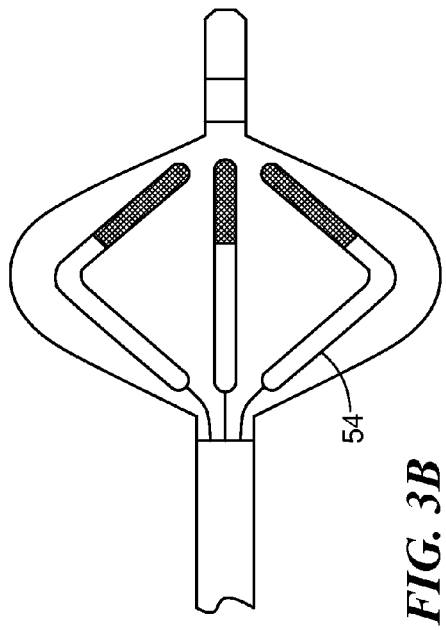
FIG. 3A-E are side view illustrations of exemplary configurations of medical devices constructed in accordance with the principles of the present invention.
Figure 3B:
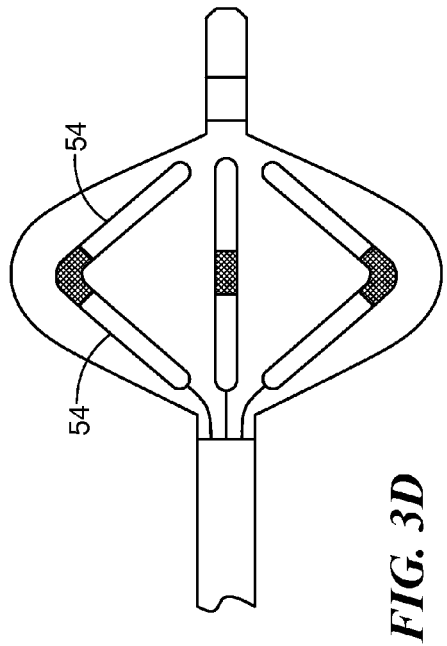
Figure 3C:
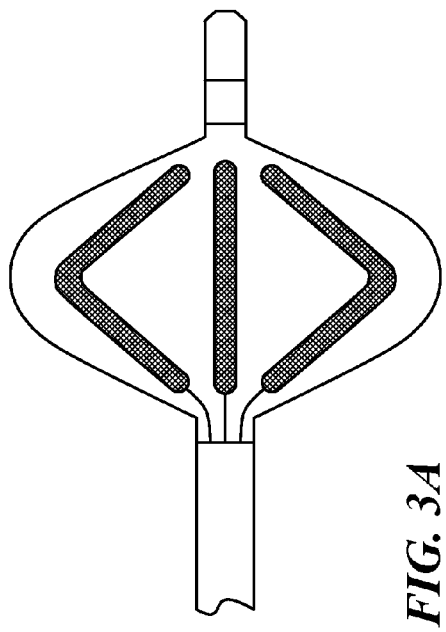
Figure 3D:
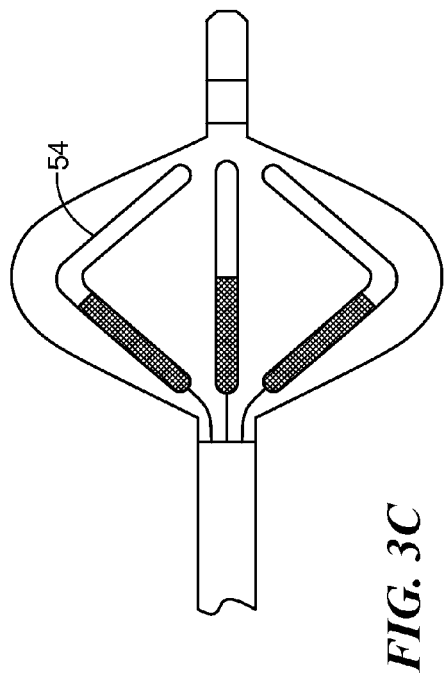
Figure 3E:
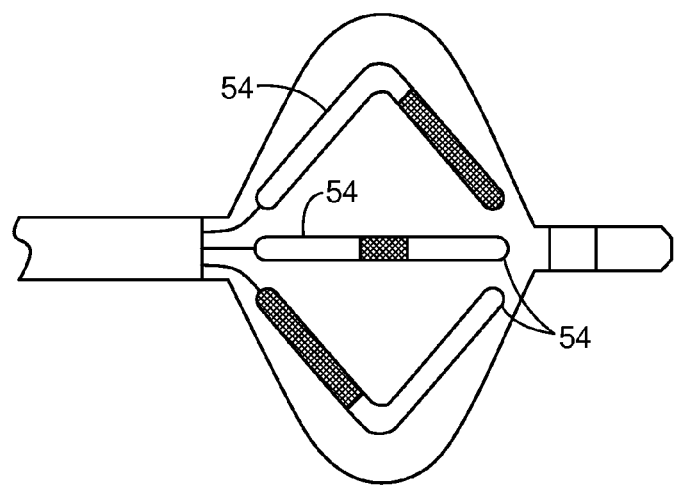

The medical device 12 is shown with greater detail in FIG. 2, and may include a handle 18, a flexible catheter shaft or elongate body 20 having a proximal end and a distal end which defines a fluid flow path, a treatment assembly which may include an expandable member 22 coupled to the elongate body 20 in fluid communication with the fluid flow path, and a diagnosis or mapping assembly including at least one electrode 24 on the treatment assembly or expandable member 22. The terms "proximal" and "distal" are generally understood in the medical device industry. For example, a catheter handle may be at a proximal end, and various components for treating a patient may be at or near a distal end. In addition, the terms "proximal" and "distal" may refer to either absolute positions on medical device(s), or may refer to relative positions along a longitudinal axis defined by medical device(s) or along a geometric path of advancement, retraction or position.

The treatment assembly may include a cryogenic element, tip, or expandable member 22, which may include one or more balloons. For example, there may be a first or inner balloon 26 inside a second or outer balloon 28. A balloon in an expanded configuration may have any suitable shape, such as for example a spherical shape or a shape with a distal conical portion 30, an intermediate portion 32, and a proximal conical portion 34. If the expandable member is a single balloon, the electrodes may be on an outer surface of the balloon. If the expandable member 22 is a double balloon treatment assembly, the electrodes 24 may be on the outer balloon. If the expandable member 22 is a double balloon configuration, the inner balloon may be in fluid communication with an inflation lumen so that it inflates to an expanded shape, and the outer balloon follows that expanded shape. The outer balloon may be provided for additional safety or leak detection. Alternatively, different types of expanding members may be provided, including for example an expandable armature or wireframe with a sheath or cover.

The wall of the expandable member 22 may be very thin, or formed with one or more suitable materials to achieve high heat transfer rates. Examples of materials that may be used to construct such an expandable member of a treatment assembly are polymers, plastics, or a mixture or layers thereof. An injection lumen 44 and an exhaust lumen 46 are in fluid communication with the interior of the expandable member 22 or balloon to define a fluid flow path therethrough, facilitating the delivery and/or circulation of a refrigerant or coolant such as a cryogenic fluid.

The electrodes 24 on the treatment assembly may provide feedback signals indicating electrical activity at the site of contact with the tissue, which may for example be myocardial tissue or an ostium of the pulmonary vein. The electrodes may be of any type, number, arrangement, configuration, or shape. For example, the electrodes 24 may have the shape of longitudinal strips. Alternately, electrodes may surround or encircle substantially all or only a small portion of the expandable member. As shown in FIG. 2, the electrodes 24 may extend between a distal position 35 and a proximal position 45 on the expandable member 22, which may extend the full or partial longitudinal length of the expandable member 22. Specifically, a distal end of the electrodes may be positioned at a distal end of the expandable member, or proximal of the expandable member distal end for ease of manufacture.

The electrodes may be in the form of conductive strips applied to the outer surface of the expandable member, which may be made of metal, conductive polymers, conductive ink printing, or micro-capillary printing. The electrodes may be adhesively bonded to the expandable member or applied by ion-deposition or plasma deposition. Alternatively, conductive materials such as for example silver, platinum or gold may be doped or otherwise mixed into the balloon material.

The electrodes may be arranged at different angular positions around a longitudinal axis of the catheter, to provide a circumferential map around the surface of the expandable member 22. In contrast with a single signal provided by a single longitudinal or annular electrode, such a detailed circumferential map gives directional information as to local electrical activity, and which portions may need treatment. Further, such a circumferential map provides information as to whether the expandable member is in the desired position for treatment, and whether the expandable member is in correct alignment to the patient's anatomy. For example, an initial map may be obtained, the results evaluated, and the medical device repositioned until a desired site for treatment is selected. The corresponding map may be used as a baseline, and the relative uniformity and continuing strength of the signals from each electrode can confirm effective contact of the expandable member with the selected tissue. In addition, variation of signal strength in a region or a side of the expandable member may indicate that the expandable member should be realigned.

The electrodes 24 may be customized to provide effective portions selected among a variety of sizes and shapes for contacting or otherwise assessing the tissue treatment area. The size, shape or length of the electrodes may be limited, for example, by covering a portion of the electrode with an insulating material. The dimensions of the electrodes may thus have an optimized configured having sufficient size and a geometric arrangement to effectively map and ablate, while avoiding excessive surface area and minimizing reception of 'noise' or other signals. Accordingly, an effective portion of the electrodes may be limited to a proximal conical portion, a distal conical portion, or both portions of the expandable member. Such an arrangement may enable a specific portion of the expandable member to map or treat specific tissues and various shapes of a patient's anatomy. Alternately, effective portions of the electrodes may be limited to different portions of the expandable member, such as for example one electrode on a proximal conical portion, another electrode on a central portion, and yet another electrode on a distal conical portion. Such differential electrode placement may aid in selecting tissue for treatment, may clarify the current positioning and alignment of the expandable member's longitudinal axis, or may provide for differential diagnosis and treatment of different longitudinal portions of the treatment assembly.

During operation, the mapping and ablation elements should be positioned in positive contact with the tissue selected for treatment. The signals obtained from the electrodes 24 may be monitored and evaluated to confirm positive contact. Arranging the electrodes 24 in different angular positions around the expandable element, for example the circumference of a balloon, enables a map of conditions around that expandable element. In other words, a physician may obtain a composite map or display of signals at a plurality of positions around the expandable element, rather than a lone signal from a single electrode or an aggregate indicator of any signal that may be present at any one position. A plurality of electrodes configured around the longitudinal axis may also indicate if the expandable element is in positive contact with the desired tissue, or if the longitudinal axis of the expandable element is aligned with that tissue. In the case of tissue selected for treatment being a lumen or other body passage such as for example a blood vessel, a plurality of electrodes around the longitudinal axis of the expandable element may also indicate if the expandable element is occluding the selected passage.

During a medical procedure, if the mapping and ablation element is not in physical contact with the desired tissue, it may be possible for another electrical signal, noise, or "far-field signal" from another region in the patient's anatomy such as the heart to propagate, for example through a medium such as blood, to the electrodes. Accordingly, limiting the electrodes to a size commensurate with obtaining acceptable mapping results may also inhibit the electrode from receiving far-field signals from sources other than the desired tissue. Positioning an effective portion of the electrodes on a specific section of the expandable member may also enable optimization of the electrodes for specific types of treatments or types of tissues for treatment. For example, positioning them on a distal portion such as a distal conical portion of the expandable member may facilitate treatment of an ostium of a blood vessel or other passage. In another example, positioning effective portions of electrodes on a central or equatorial section of the expandable member may enable treatment of a larger ostium. Similarly, positioning effective portions of electrodes on a proximal portion such as a proximal conical portion of the expandable member may facilitate treatment of a distal-opening ostium or the distal surface of a septal opening. Alternately, positioning effective portions of electrodes on different sections of the expandable element may enable diagnosis of the tissue and assist in selecting tissue for treatment, or may provide further information on the current placement, alignment, and positive contact of the expandable element with the patient's anatomy.

Figure 4:
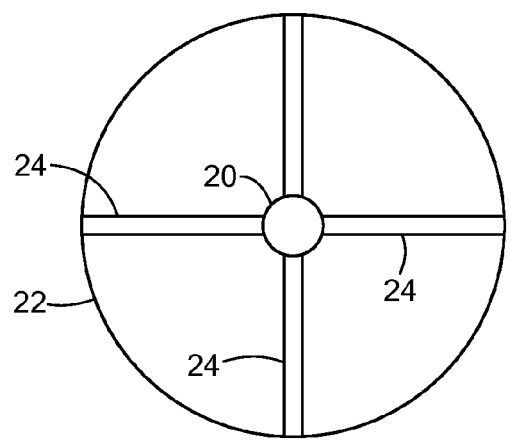
FIG. 4 is a end view illustration of another exemplary medical device constructed in accordance with the principles of the present invention.
Figure 5:
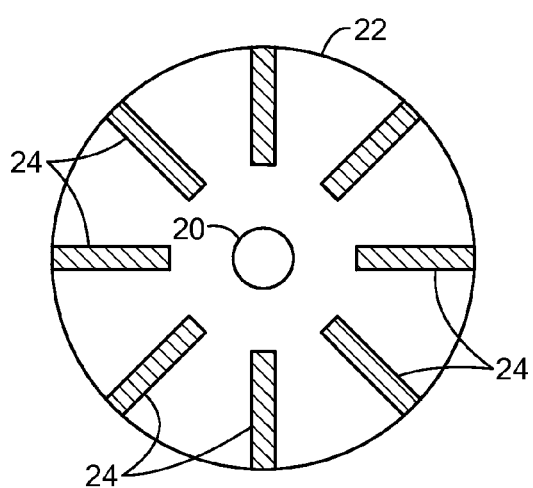
FIG. 5 is a end view illustration of yet another exemplary medical device constructed in accordance with the principles of the present invention.

The number of electrodes 24 may be selected with a view toward the types of tissue to be mapped, the character of map that is desired, or for example to match the type of map and number of electrodes provided on a dedicated mapping device such as a mapping catheter. For example, by increasing the number of mapping electrodes on the expandable member, or by reducing the width of each electrode, maps may be obtained with greater precision and fidelity. Specifically, four electrodes are shown in FIG. 4, and eight electrodes are shown in FIG. 5, but any suitable number of electrodes may be provided. For example, the number of electrodes may range from one to a multitude, or even a mesh of filament electrodes.

The electrodes should be in electrical communication with some device for obtaining, evaluating and perhaps recording a signal from each electrode. Such devices may include for example an electrocardiograph ("ECG") box 42, console 14 and a display. Electrical communication may be provided by wires or other conductive elements, which may pass from each electrode along a suitable path to the electrical devices, such as for example a lumen defined by the elongate body or embedded within a wall of the elongate body.

The handle 18 of the medical device may be equipped with input ports for an electrical connector, a coolant injection tube connector, and a return tube connector. These connect via various internal junctions or tubes passing through the handle to provide these three functions to the distal tip of the catheter. The handle may also include various control assemblies, such as for example steering actuators for manipulating steering elements such as pull wires to direct and steer portions of the shaft body and the treatment assembly. The handle may further include one or more switches, sensors, valves, as well as safety detection or shut down elements (not illustrated).

Umbilical system 16 may include three separate umbilicals: a coaxial umbilical 36, an electrical umbilical 38 and a vacuum umbilical 40. Although separate umbilicals are shown, it is contemplated that one or more connections may be included in one or more umbilicals having one or more coaxial or otherwise integrally contained passages or conduits therethrough providing electrical and fluid communication between the medical device 12 and the console 14. If the user wishes to perform a radiofrequency ("RF") ablation procedure, radiofrequency energy can be provided to electrodes on the medical device 12 via electrical umbilical 38 to perform an RF ablation. In addition, electrical umbilical 38 can include the ECG box 42 to facilitate a connection from one or more electrodes on the medical device 12 to an ECG monitor (not shown). Coaxial umbilical 36 may include both a cooling injection umbilical and a vacuum umbilical that provide respective inlet and return paths for a refrigerant or coolant used to cool a tissue-treating section of the device 12. The vacuum umbilical 40 may provide a safety conduit allowing excess coolant or gas to escape from the medical device 12 if the pressure within the medical device 12 exceeds a predefined limit. The vacuum umbilical 40 can also be used to capture air through a leak of the outer vacuum system where it is outside the patient and as a lumen to ingress blood when inside the patient.

The medical system 10 may also include one or more sensors to monitor the operating parameters throughout the system, including for example, pressure, temperature, flow rates, volume, or the like in the console 14, the umbilical system 16, and/or the medical device 12.

Now referring to FIG. 2, the medical device 12 may include an elongate body 20 which can navigate through a patient's vasculature or other body passages. The elongate body 20 may define a proximal portion and a distal portion, and may further include one or more lumens disposed within the elongate body 20, thereby providing mechanical, electrical, and/or fluid communication between the proximal portion of the elongate body 20 and the distal portion of the elongate body 20. For example, the elongate body 20 may include the injection lumen 44 and the exhaust lumen 46, defining a fluid flow path therethrough. In addition, the elongate body 26 may include a guidewire lumen 48 disposed within and/or extending along at least a portion of the length of the elongate body 20 for over-the-wire applications.

The elongate body 20 of the medical device 12 defines a proximal end 50 and a distal end 52, a handle 18 affixed to the proximal end, and one or more treatment regions for energetic or other therapeutic interaction between the medical device 12 and a treatment site. A treatment region or element may provide, for example, radiofrequency energy, cryogenic therapy, or the like. The medical device may include a treatment region having a thermal treatment element disposed on the elongate catheter body 20 at or near its distal end 52 to provide any of the above-named energetic treatments.

Referring to FIGS. 3A-3E, a variety of different arrangements and quantity of electrodes may be provided on a treatment assembly such as a balloon. If desired, the wider central portion may be used for mapping, or some combination of distal, central, and proximal portions. The electrodes may be physically sized to obtain mapping signals on the desired portions of the balloon, or an insulating material 54 may be used to create effective portions of the electrodes. Specifically, the effective portion of the illustrated electrodes is as follows: the full length of the electrodes in FIG. 3A, a distal portion of the electrodes in FIG. 3B, a proximal portion of the electrodes in FIG. 3C, and a central portion of the electrodes in FIG. 3D, and a variety of portions of the electrodes on different portions of the balloon in FIG. 3E.

Figure 6:
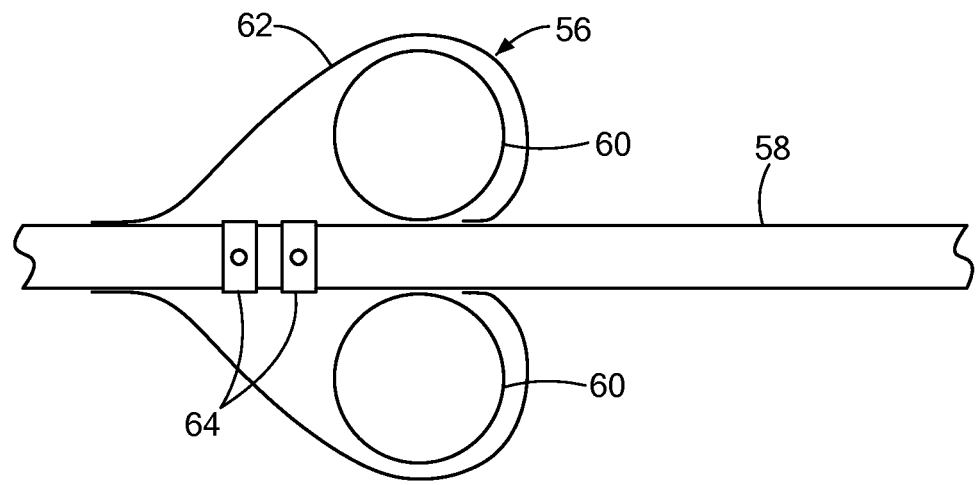
FIG. 6 is a side view illustration of another exemplary medical device constructed in accordance with the principles of the present invention.

Referring to FIG. 4-6, the medical device 56 may include a shaft 58 and a treatment assembly including an expandable member with an inner balloon 60 and an outer balloon 62. The inner balloon 60 may be toroidal in shape, and the outer balloon 62 may have a heart-shape in cross-section.

The medical device may further include a system to detect a leak of fluid and respond accordingly. Upon detection of a leak in a component of the medical system, the console may be provided with one or more systems to deliver the desired response, such as an alarm or other indication of an undesirable condition, automatically shut off delivery of cryogenic fluid, etc. For example, in the case of an expandable member with an inner balloon and an outer balloon, one or more parameters may be monitored, such as fluid volume or pressure between the inner balloon and the outer balloon. A vacuum or neutral pressure may be maintained between the inner and outer balloons, and a change in the measured parameter which exceeds a predetermined threshold may trigger the desired response.

Another example leak detection system may include one or more leak detection elements 64 provided inside the expandable member. More specifically, leak detection element(s) may be positioned inside an inflatable balloon, or in the case of double balloons the leak detention elements may be inside the inner balloon, outer balloon, or both. As shown in FIG. 6 for example, a pair of leak detection elements 64 may be coupled to the exterior of a distal portion of the outer body. The leak detection elements 64 may surround at least a portion of the expandable element or the inner body, and at least a portion of the leak detection elements 64 may be electrically conductive. The leak detection element(s) may be in fluid communication with the fluid injection lumen, exhaust lumen, and/or the fluid path. The leak detection element(s) may provide an electrically conductive electrode or the like disposed within the injection lumen, the expandable element, etc. Another example of leak detection may define a mesh or wire structure that is configurable into a plurality of geometric configurations, shapes, and or dimensions, such as an openwork fabric or structure, an interconnected network of wire-like segments, a sheet of material having numerous apertures and/or portions of material removed, or the like. In addition, the leak detection elements 64 may be constructed from a combination of elastic materials, non-elastic materials, and/or shape-memory materials, such as a nickel-titanium alloy or the like, for example. The leak detection elements 64 may include an insulated length of wire, and a portion of the wire insulation may be stripped to provide electrical conductivity at a desired position.

Figure 7:
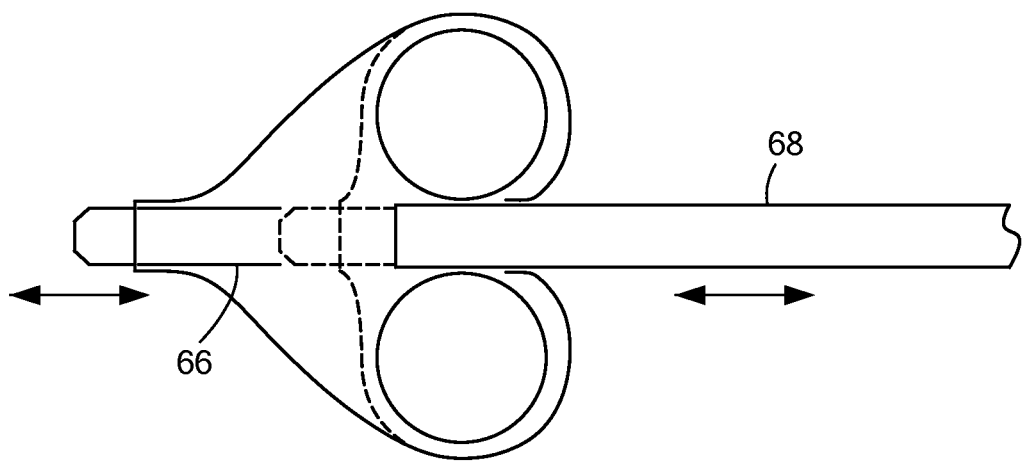
FIG. 7 is a side view illustration of yet another exemplary medical device constructed in accordance with the principles of the present invention.

In addition, the medical device may include a mechanism to change the shape or size of the expandable element. As shown in FIG. 7 for example, a medical device having a treatment assembly such as an inner balloon and an outer balloon may be affixed to a catheter shaft having an inner elongate member or body 66 and an outer elongate member or body 68, at least one of which may be adjusted or moved longitudinally with respect to the other member. An actuator element 70 may be provided on the handle that is movably coupled to a proximal portion of the catheter shaft and/or the handle, and may further be coupled to a proximal portion of the guidewire lumen or inner body 66. Accordingly, manipulating the actuator element 70 may cause the inner body 66 to slide towards either of the proximal or distal portions of the outer body.

As different portions of the expandable member may be coupled to the inner body and outer body respectively, manipulation of the actuator element may cause the expandable member 22 to be tensioned or loosened, depending on the direction of movement of the actuator element. Accordingly, the actuator element may be used to provide tension on the expandable member 22 during a particular duration of use of the medical device 12, such as for example during a deflation sequence. In addition, the actuator element 70 may be used in controlling a particular geometric configuration and/or dimension of the expandable member, i.e., the actuator element 70 may exert a tensile force on the expandable member 22 to provide for an elongated shape. Subsequently, the actuator element 70 may be retracted to allow the expandable member 22 to assume a different, broader, or spherical shape having a larger radius than that of the elongated shape experienced under tension.

The actuator element 70 may include a thumb-slide, a push-button, a rotating lever, or other mechanical structure for providing a movable coupling to the outer body, the handle, and/or the inner body. Moreover, the actuator element 70 may be movably coupled to the handle such that the actuator element is movable into individual, distinct positions, and is able to be releasably secured in any one of the distinct positions. Similarly, the actuator element 70 may include a spring-loaded mechanism or other device which is biased towards certain positions or configurations. The medical device 12 may further include indicia located on the handle element in proximity to each distinct position in which the actuator element may be located, where the indicia may directly correspond to a given dimension and/or shape the expandable element resulting from the particular position of the actuator element.

A thermocouple or other sensor may be positioned on or within the treatment assembly to sense temperature, and a plurality of electrodes may be positioned near the treatment assembly for use in mapping and/or detecting cardiac signals. Other structures within the medical device may include torque or steering wires, or other elements conventional in the art for navigation of the catheter past branch points in vessels, and for urging the treatment assembly into contact with selected tissue once its position is confirmed.

In an exemplary system shown in FIG. 1, a fluid supply 72 including a coolant, cryogenic refrigerant, or the like (in a liquid and/or a gas state), an exhaust or scavenging system (not shown) for recovering or venting expended fluid for re-use or disposal, as well as various control mechanisms for the medical system may be housed in the console. In addition to providing an exhaust function for the catheter fluid supply, the console 14 may also include pumps, valves, controllers or the like to recover and/or re-circulate fluid delivered to the handle, the catheter shaft, and distal end of the medical device. A vacuum pump 74 in the console 14 may create a low-pressure environment in one or more conduits within the medical device so that fluid is drawn into the conduit(s) of the shaft, away from the treatment assembly and towards the proximal end of the shaft. The console may include one or more controllers, processors, and/or software modules containing instructions or algorithms to provide for the automated operation and performance of the features, sequences, or procedures described herein.

Figure 8:
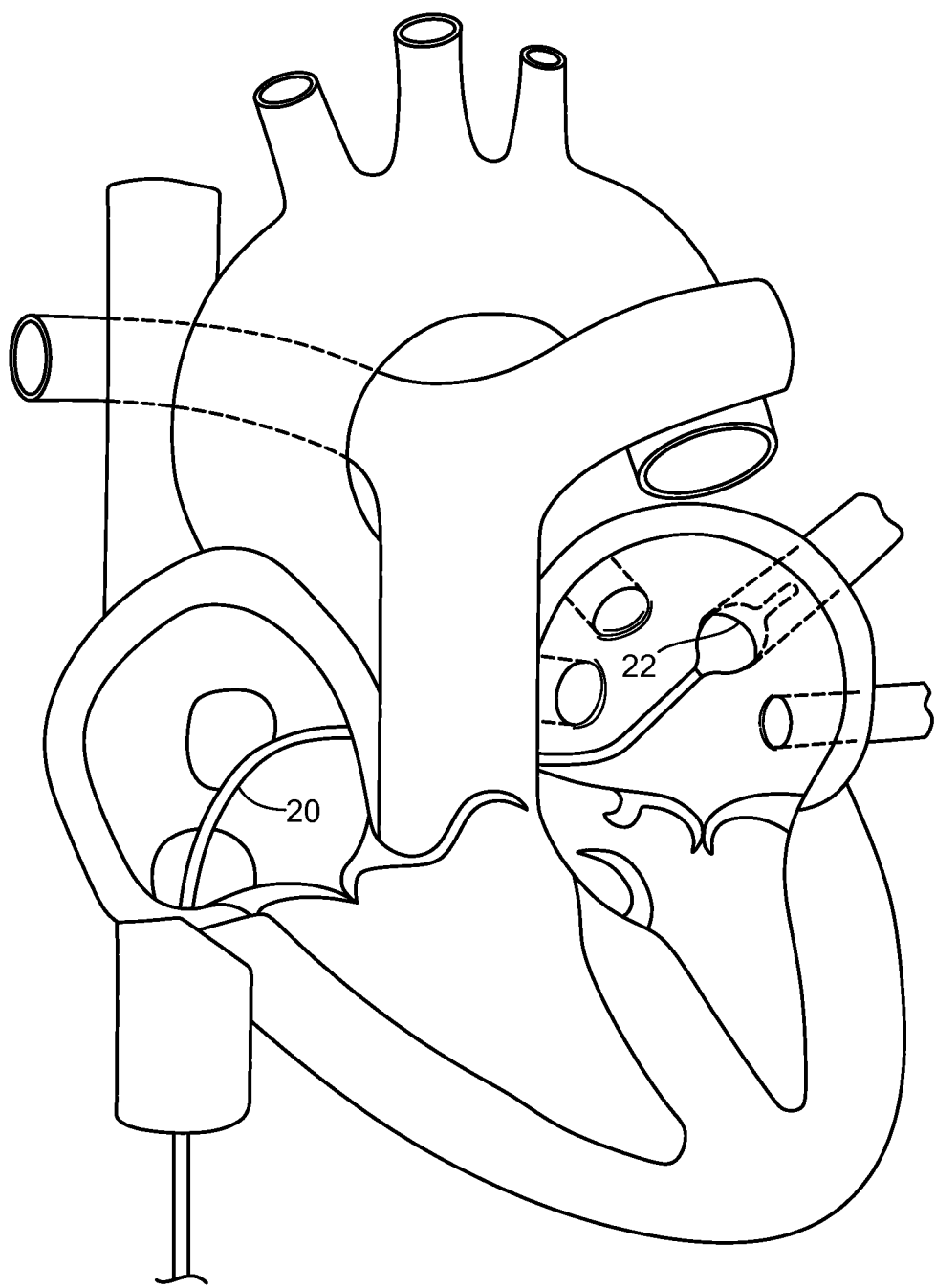
FIG. 8 is an illustration of an exemplary use of a medical device in accordance with the principles of the present invention.
Figure 9:
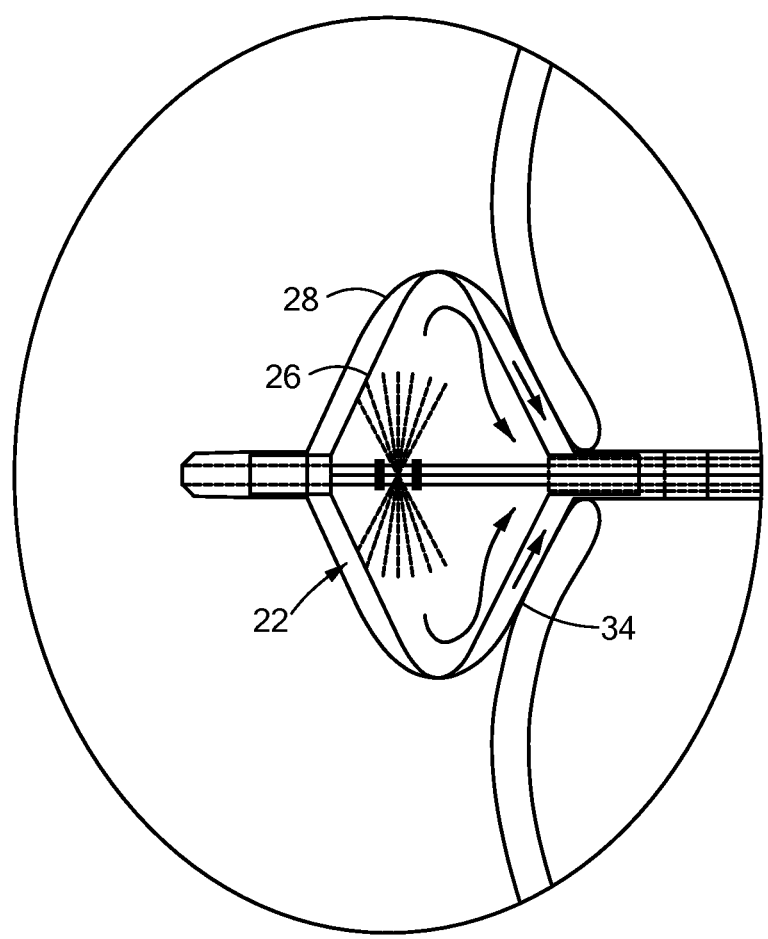
FIG. 9 is an additional illustration of an exemplary use of a medical device in accordance with the principles of the present invention.
Figure 10:
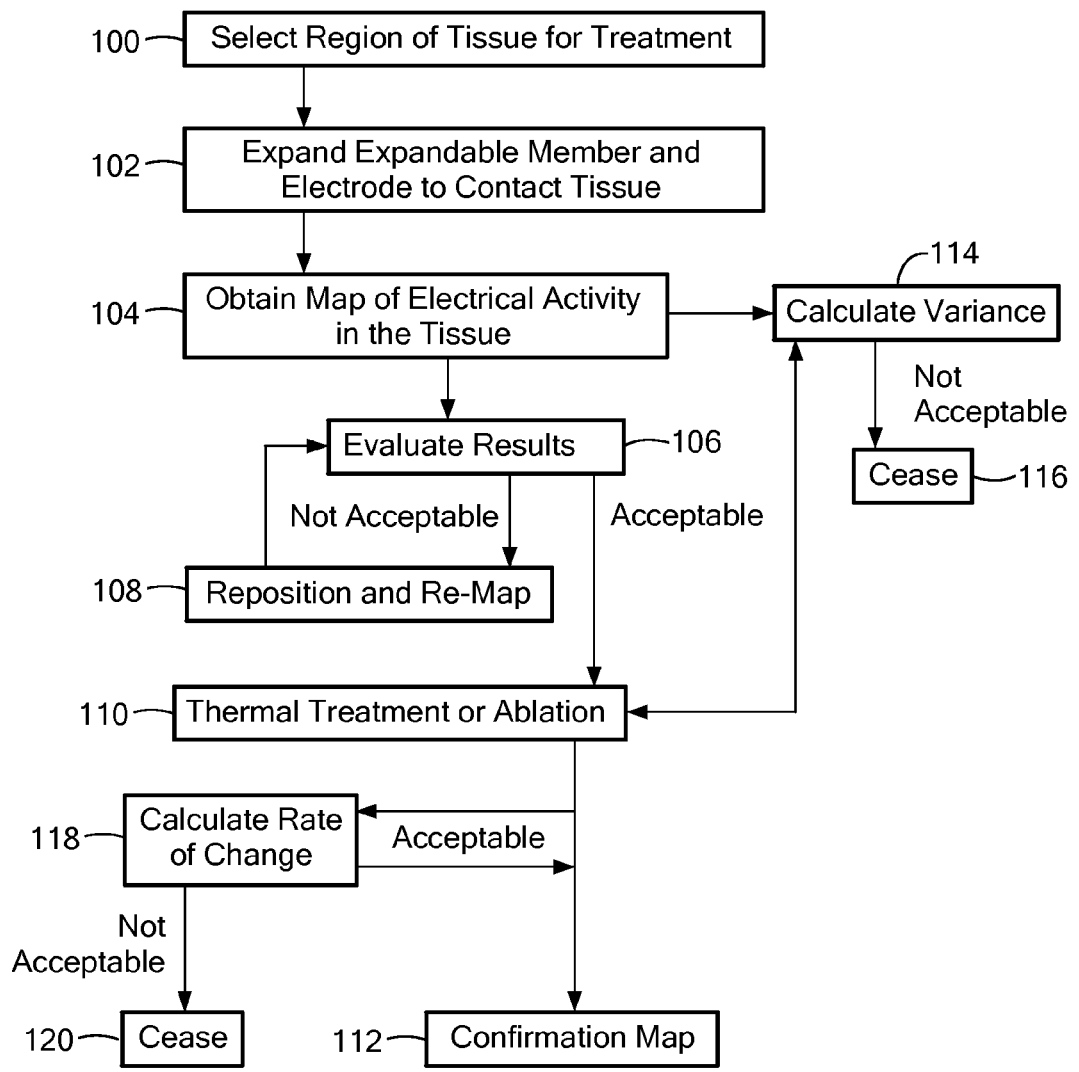
FIG. 10 is a flow chart in accordance with the principles of the present invention.

Now referring to FIGS. 8 and 9, exemplary uses of the system 10 are shown. A method of medical treatment is also illustrated in FIG. 10, which may include selecting a region of tissue for treatment (step 100); expanding an expandable member 22 and an electrode 24 on the expandable member into contact with tissue to be treated (step 102); obtaining a map of electrical activity in the tissue by gathering signals from the electrode (step 104); evaluating the results (step 106); either confirming the current position or repositioning and re-mapping (step 108); performing thermal treatment or ablating the tissue by energy transfer between the expandable member and the tissue (step 110); and obtaining a signal from the electrodes 24 to evaluate electrical activity in the tissue with a confirmation map (step 112). In particular, the treatment assembly of the medical device 12 may be positioned in proximity to or otherwise adjacent to a target tissue region to be treated. The introduction and positioning of the medical device 12 within the patient may include a percutaneous approach from the groin through femoral vein, the femoral artery, or other access point and into a desired region or anatomy, such as a chamber of the heart or other vasculature. Alternatively, the medical device may be introduced and positioned within the patient through a sub-xiphoid incision or one or more small thoracotomy incisions or other surgical access techniques. The introduction and positioning can be guided by use of visualization, imaging and dissection techniques, including, for example, fluoroscopy imaging in an intravascular procedure and/or video thoracoscope in a minimally invasive surgical procedure.

Once the medical device has been positioned in the vicinity of the tissue to be treated, the expandable member 22 may be expanded (step 102) to place a treatment surface of the treatment assembly into contact with the selected tissue region, which may include cardiac tissue for example, or the ostium of a pulmonary vein. When the selected tissue is in the region of an ostium, expanding the balloon into contact may limit or obstruct flow of bodily fluids such as blood, which will improve efficiency of heat transfer between the tissue and the treatment assembly. Expansion of the balloon may include inflating a balloon such as the inner balloon with an inflation medium, or by structurally expanding an armature or other expandable member. The treatment surface may be a distal portion of an expandable member, such as the distal conical portion 30 of the balloon shown in FIG. 8. Alternate treatments may include passing a treatment assembly through a septal opening or puncture, and placing a proximal conical portion 34 of the balloon into contact with the distal surface of the selected tissue, as shown in FIG. 9. An expandable member may facilitate sufficient or optimal contact with the tissue, as compared to an ablation element having a fixed geometry or size. After expansion, the medical device may be urged in the appropriate longitudinal direction to improve contact of the expandable member with selected tissue such as an ostium. Manipulation of the treatment assembly may include steering or deflecting at least a portion of the medical device catheter shaft, using any suitable steering system such as the actuator on the handle.

Upon reaching the desired region of anatomy and the desired configuration of the treatment assembly, electrophysiological mapping (step 104) may be performed using the electrodes on the balloon to obtain a baseline map of electrical activity in the tissue. The results of the mapping procedure may be presented to the physician using a suitable mechanism such as a display. For example, the signal from each electrode may be presented individually and/or collectively. The characteristics of each signal may be indicated in a graphic or visual display, may include indications of the local geometry, shape or arrangement of the electrodes, and/or a representation of the patient's anatomy near the mapping elements. Differences in amplitude, relative timing, deviations, comparisons to a pacing signal, relative changes, rates of change, variance, and other suitable characteristics may also be presented to the physician.

The quality of the mapping may be enhanced by providing the medical system with a plurality of electrodes arranged in different angular positions around a longitudinal axis of the expandable member, because the map can display both electrophysiological and geometric information, graduations of all characteristics of the signals described above, variations of the electrical activity in different local areas of the patient's anatomy, and changes in one or more signals over time. The map display may include individual waveforms, an aggregate display, an overlay of multiple signals to indicate aberrations, etc. It may include highlights of certain characteristics, numerical parameters, color indications, animations, warnings, etc. The map display may have a 2-D or 3-D representation of the patient's anatomy, the medical device or the electrodes, and/or the electrical activity. The map display may also indicate changes in one or more signals over time, variations among the signals, and relative differences of electrical activity in one area relative to the others.

In addition, the medical system may also calculate the current variance (step 114) of each electrode's signal or an aggregate such as an average variance for all the signals. Additional characteristics may be calculated and evaluated, including the standard deviation of the signals. For example, a low variance among the signals before or during ablation may indicate that the expandable member has sufficient contact with the selected tissue, for example that the expandable member is contacting the full circumference of an ostium, that the expandable member longitudinal axis is aligned with the local anatomy, and accordingly that an ablation will likely be successful. If the variance for a signal or group of signals before or during ablation is relatively high, it may indicate that the expandable member has insufficient contact with the selected tissue, for example that the expandable member is not contacting the full circumference of an ostium, that the expandable member longitudinal axis is not aligned with the local anatomy, and accordingly that an ablation may not be successful. Accordingly, if the variance exceeds a predetermined threshold, it may similarly suggest that ablation energy should cease (step 116), the ablation element should be repositioned to obtain sufficient contact with the selected tissue and/or realigned with the patient's anatomy.

After obtaining an electrophysiological map, diagnosing aberrant tissue and selecting a target site for ablation, the treatment assembly may be used to thermally treat the targeted tissue (step 110). For example, refrigerant or coolant from the fluid supply/coolant source may be directed to the balloon through the injection lumen. The cryogenic procedure may be performed by dispensing a specific predetermined volume of refrigerant from the source of cryogenic fluid. Upon departure from the injection lumen, the refrigerant (or substantial portion thereof) may undergo two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to a desired temperature. The expanded refrigerant is then directed away from the balloon by the exhaust lumen. The goal of such ablation may be to cease the aberrant electrical activity in that tissue, which may be confirmed by confirming that a signal from at least one electrode in contact with that tissue has decreased to zero amplitude.

During an ablation procedure and/or following ablation for example by cryogenic treatment, the medical device 12 may be used to obtain another electrophysiological map to confirm the results of the ablation procedure (step 112). The medical system 10 may continue to provide or display information relating to the signals from the electrodes 24, during delivery of the ablation energy. While ablation energy is being delivered, the signals from the electrodes may diminish to zero, indicating a likely successful ablation. During the ablation, the medical system may simultaneously monitor and continuously evaluate the signals from the electrodes.

For example during ablation, the medical system may calculate the current rate of change (step 118) of each electrode's signal or an aggregate such as an average rate of change for all the signals. If the rate of change for a signal or group of signals during ablation meets or exceeds a predetermined threshold, such that they are approaching zero within expectations, it may suggest that the ablation is likely to succeed and should continue until completion. If the rate of change for a signal or group of signals during ablation is below a predetermined threshold, it may suggest that ablation energy should cease (step 120), and the ablation element should be repositioned to obtain sufficient contact with the selected tissue and/or realigned with the patient's anatomy.

Following ablation, if the confirmation map indicates the ablation procedure was successful, the medical treatment may be concluded and the medical device 12 removed from the patient. If the confirmation map indicates the ablation was insufficient, an additional ablation may be conducted with the same medical device 12 in the same position.

By providing an integrated medical system and medical device capable of performing both mapping and ablation without adjusting the position of the treatment assembly, more accurate mapping, more precise positioning of the ablation element and clear confirmation of the results may be obtained. In addition, a single medical device may be used to conduct the mapping, ablation, and confirmation mapping, thereby reducing complexity and cost, eliminating a requirement for a separate mapping device and ablation device, and improving patient outcomes.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
    an elongate body defining a fluid flow path;
    an expandable member coupled to the elongate body in fluid communication with the fluid flow path, the expandable member having a distal portion and a proximal portion;
    a cryogenic fluid source in fluid communication with the fluid flow path and the expandable member, delivery of the cryogenic fluid into the expandable member reducing the temperature of the expandable member to at least one of cool and ablate tissue in contact with the expandable member; and
    a plurality of electrodes on the expandable member, each of the plurality of electrodes being an elongate strip having a length that extends between the distal portion of the expandable member and the proximal portion of the expandable member, the length of each electrode being configured to both transmit ablation energy to ablate tissue in contact with the electrode and receive electrical signals from tissue in contact with the electrode to obtain a map of electrical activity in the tissue.

2. The medical device of claim 1, wherein the expandable member is a balloon.

3. The medical device of claim 2, wherein the balloon in an expanded configuration has a shape with a distal conical portion and a proximal conical portion.

4. The medical device of claim 1, wherein the expandable member includes a first balloon inside a second balloon, the electrodes being on the second balloon.

5. The medical device of claim 1, wherein the electrodes are arranged at different angular positions around a longitudinal axis of the expandable member.

6. The medical device of claim 1, wherein a distal end of each electrode is proximal of a distal end of the expandable member.

* * * * *